United States Patent [19]

Leroi et al.

[11] 4,036,703

[45] July 19, 1977

[54] METHOD OF SEPARATING CHLORINATED ALIPHATIC HYDROCARBONS WITH 1 TO 3 CARBON ATOMS FROM MIXTURES THEREOF BY EXTRACTIVE DISTILLATION

[75] Inventors: Jean-Claude Leroi, Villeurbanne; Francois Vachet, Decines, both of France

[73] Assignee: Rhone-Poulenc Industries, Paris, France

[21] Appl. No.: 697,200

[22] Filed: June 17, 1976

[30] Foreign Application Priority Data

June 25, 1975 France ................................. 75.19892
Apr. 23, 1976 France ................................. 76.12120

[51] Int. Cl.$^2$ .......................... B01D 3/40; C07C 17/38
[52] U.S. Cl. ............................................. 203/57; 203/58; 203/60; 203/62; 203/63; 260/652 P; 260/654 S; 203/73; 203/78
[58] Field of Search .................... 260/652 P, 654 S; 203/57, 58, 60, 61, 62, 63; 203/51, 61, 91, 73

[56] References Cited

U.S. PATENT DOCUMENTS

| 3,113,079 | 12/1963 | Bergeron et al. | 203/58 |
| 3,658,657 | 4/1972 | Bursack et al. | 203/60 |
| 3,658,658 | 4/1972 | Bursack et al. | 203/60 |
| 3,869,353 | 4/1975 | Schubert | 203/60 |

FOREIGN PATENT DOCUMENTS

684,577  12/1952  United Kingdom .................. 203/62

Primary Examiner—Wilbur L. Bascomb, Jr.

[57] ABSTRACT

A method of partially or totally separating chlorinated aliphatic $C_1$ to $C_3$ hydrocarbons from mixtures of at least two of the chlorinated hydrocarbons by extractive distillation.

The mixture of the chlorinated hydrocarbons is distilled in the presence of one or more third organic compounds having a boiling point higher than that of the substances to be separated, selected from the group comprising methyl, ethyl, normal propyl and isopropyl mono and di-chloroacetates; benzyl alcohol; salicylaldehyde, benzaldehyde, n-heptanal, methylisobutylketone, tetramethylurea, $\gamma$-butyrolactone; normal propyl, isopropyl, normal, secondary and tertiary butyl acetylacetates; diethyl oxalate, dimethyl succinate and preferably methyl and ethyl acetylacetates; acetic anhydride, N-formyl-morpholine, 2-chloro ethanol, hexamethylphosphotriamide, dimethyl sulphate and normal tributyl and triisobutyl phosphates.

This method is particularly applicable to separation of mixtures of 1,1,1-trichloro ethane and 1,2-dichloro ethane; trichloroethylene and 1,2-dichloro ethane; perchloroethylene and 1,1,2-trichloro ethane; and carbon tetrachloride and 1,2-dichloro ethane.

13 Claims, No Drawings

METHOD OF SEPARATING CHLORINATED ALIPHATIC HYDROCARBONS WITH 1 TO 3 CARBON ATOMS FROM MIXTURES THEREOF BY EXTRACTIVE DISTILLATION

The invention relates to a method of partially or totally separating chlorinated aliphatic $C_1$ to $C_3$ hydrocarbons from mixtures of at least two of these compounds by extractive distillation.

Mixtures of some chlorinated aliphatic hydrocarbons with up to 3 carbon atoms, and more particularly mixtures of trichloroethylene with 1,2-dichloro ethane, perchloroethylene with 1,1,2-trichloro ethane, carbon tetrachloride with 1,2-dichloro ethane, and 1,1,1-trichloro ethane with 1,2-dichloro ethane, are very difficult to separate by conventional fractional distillation, either because of the formation of azeotropic mixtures or because of the low volatility of the constituents of such mixtures.

Separation of trichloroethylene from 1,2-dichloro ethane, for example, is extremely important in units manufacturing vinyl chloride and chlorinated aliphatic $C_2$ and/or $C_1$ hydrocarbons as solvents.

It is known that 1,2-dichloro ethane and trichloroethylene have boiling points very close to one another (83.65° and 86.2° C respectively) and that they form an azeotropic mixture with 62 molar % of 1,2-dichloro ethane distilling at 82.2° C under atmospheric pressure. It is practically impossible to separate any mixtures of these two substances into pure products by conventional distillation. It is equally impossible to envisage a method of distillation in two columns operating at different pressures, for the azeotropic mixture is of a composition which is virtually constant and dependent on pressure.

In the case of mixtures of 1,1,1-trichloro ethane with 1,2-dichloro ethane, separation of 1,1,1-trichloro ethane (bp 74°–75° C) from 1,2-dichloro ethane (bp 83°–84° C) by simple distillation becomes more difficult as the proportion of 1,1,1-trichloro ethane in the mixtures increases, due to the low volatility of 1,1,1-trichloro ethane relative to 1,2-dichloro ethane. Thus satisfactory separation of 1,1,1-trichloro ethane from mixtures in which it is present in an amount over 90% by weight would necessitate a distillation column of over 150 trays, which in practice would involve using several, at least 4, columns. This obviously impractical since it would make the separating process expensive.

It is also known that in some separating processes which are difficult to carry out by simple distillation, as is the case, e.g., when separating butene from butane, butene from butadiene, or benzene from cyclo hexane, extractive distillation may be applied in the presence of a suitably selected third substance. In fact, some specific substances affect the feasibility of distillation and enable them to be separated.

These third substances obviously vary according to the nature of the mixtures to be separated and, when confronted with a problem of separating given substances, it is almost impossible to foresee which third substances would be suitable.

Applicants have thus discovered a group of third substances which, if incorporated in mixtures of chlorinated aliphatic $C_1$ to $C_3$ hydrocarbons, will enable them to be partially or totally separated in a simple and efficient manner.

According to the invention, the mixtures to be separated are distilled in the presence of one or more organic compounds having a boiling point higher than that of the substances to be separated, selected from the group comprising methyl, ethyl, normal propyl and isopropyl, mono and di-chloroacetates; benzyl alcohol; salicylaldehyde, benzaldehyde, n-heptanal, methylisobutylketone, tetramethylurea and γbutyrolactone; normal propyl, isopropyl and normal, secondary and tertiary butyl acetylacetates; diethyl oxalate, dimethyl succinate and preferably methyl and ethyl acetylacetates; acetic anhydride, N-formylmorpholine, 2-chloro ethanol, hexamethylphosphotriamide, dimethyl sulphate and normal tributyl and triisobutyl phosphates.

In the special case of extractive distillation of a binary mixture, the organic third compound passes entirely to the bottom of the column with one of the substances or a mixture in which said substance is present in high concentration, the other substance or a mixture containing a high concentration of the second substance being present in the distillate.

The liquid from the bottom of the column can then easily be treated in a second column, where the organic third compound can be regenerated by conventional fractional distillation.

The proportion of organic third compound to be injected into a column for extractive distillation of a mixture of chlorinated aliphatic $C_1$ to $C_3$ hydrocarbons varies, since it is a function of several factors such as: the effectiveness of the organic compound selected, the size of the column (number of trays), and the selected conditions (reflux rate, pressure). The proportion is generally at least 10% by weight and preferably in the range of at least equal to the weight of the mixture of chlorinated hydrocarbons to three or more times the weight of the mixture, although it is not desirable unnecessarily to increase the quantity of organic third compound. This is generally regenerated by conventional fractional distillation once it has fulfilled its function as a third solvent or component for extracting the chlorinated aliphatic $C_1$ to $C_3$ hydrocarbons.

The method of the invention may generally be applied to mixtures in any proportions of chlorinated aliphatic $C_1$ to $C_3$ hydrocarbons.

In order to simplify the process, substances which can easily be separated from mixtures encountered in industrial installations are generally removed first, leaving behind mixtures of the pairs of substances which are difficult to separate, in greatly preponderant proportions, for treatment by the method of the invention.

Special examples of mixtures which are difficult to separate, apart from mixtures including or essentially consisting of 1,2-dichloro ethane and trichloroethylene on the one hand and 1,1,1-trichloro ethane and 1,2-dichloro ethane on the other, include mixtures of perchloroethylene with 1,1,2-trichloro ethane and of carbon tetrachloride with 1,2-dichloro ethane.

According to the invention, extractive distillation may be carried out either at a pressure below atmospheric, more particularly under partial or high vacuum, or preferably at atmospheric pressure. In an advantageous embodiment of the invention, the organic third compound is recovered at a pressure below that used for the extractive distillation proper.

According to the invention, the mixture which is submitted to extractive distillation is introduced into a distillation column, preferably into the lower third of the column, and the organic third compound is introduced into the upper part or the top. One of the two substances to be separated is collected at the top. The second substance passes to the bottom of the column in admixture with the organic third compound. It is directed to a second column and recovered, pure, from the top, while the organic third compound is withdrawn from the bottom and is recycled to the first column.

Either the disappearance of the azeotropic mixture or the change in the relative volatility of the constituents of themixture, as the case may be, in the presence of an organic third compound, may be checked by continuously feeding into a still a mixture comprising the substances to be separated — having the composition either of an azeotropic mixture thereof or of a mixture difficult to separate — and the selected organic third compound. The mixture is then continuously heated and partially vaporized and the vapor-liquid mixture separated in an equilibrium cell; the vapor emerging at the top is collected after condensation, while the liquid phase is recovered from the bottom of the cell.

In instances where the organic compound selected is ineffective for separation, the two substances to be separated will remain in the same relative proportion in the two effluents collected, and this proportion will be the same as in the original mixture.

On the other hand, when the selected organic third compound breaks or greatly shifts the azeotropic mixture or, as the case may be, alters the feasibility of distilling a substance A mixed with a substance B, the relative proportion will be different in the two effluent phases, and the "pseudovolatility" $\alpha$ of substance A relative to substance B may be defined by the equation:

$$\alpha = \frac{\% \text{ by weight of A}/\% \text{ by weight of B in vapor phase}}{\% \text{ by weight of A}/\% \text{ by weight of B in liquid phase}}$$

substance A being that which has increased in proportion to the original mixture in the vapor phase collected.

The following examples are given by way of illustration and not by way of limitation:

EXAMPLE 1

In a first distillation column 32 mm in diameter, comprising 60 actual trays, operating at atmospheric pressure, 117 g/hour of a boiling liquid mixture consisting of 2.76 parts by weight of 1,2dichloro ethane and 97.24 parts of 1,1,1-trichloro ethane is introduced into the lower third part of the column. 763 g/hour of acetic anhydride, at 90° C, is introduced at about the top. The reflux rate is 1.5. The product at the top is made up of:
  112.82 g/hour of 1,1,1-trichloro ethane
  0.12 g/hour of 1,2-dichloro ethane
  0.36 g/hour of acetic anhydride.
  The effluent from the bottom of the still consists of:
  3.1 g/hour of 1,2-dichloro ethane
  0.96 g/hour of 1,1,1-trichloro ethane
  762.64 g/hour of acetic anhydride.

The effluent is fed to a second column operating at atmospheric pressure and comprising 15 trays.

At the top of this column 5.1 g/hour of a mixture is collected, in the following proportions:
  3.10 g/hour of 1,2-dichloro ethane
  0.96 g/hour of 1,1,1-trichloro ethane
  1.04 g/hour of acetic anhydride The acetic anhydride recovered from the bottom of the column contains only 1,2-dichloro ethane, a quantity below the detection limit of the analytic methods used (100 parts per million). This anhydride is recycled to the first distillation column.

EXAMPLE 2

A mixture of acetic anhydride, 1,1,1-trichloro ethane and 1,2-dichloro ethane of the following composition by weight:

| acetic anhydride | : 70 % | |
| 1,1,1-trichloro ethane | : 29.4% | (weight ratio 1,1,1-(trichloro ethane/ (1,2-dichloro ethane |
| 1,2-dichloro ethane | : 0.6% | ( = 49/1. | is placed in a still and partially vaporized. The vapor-liquid mixture is then separated in an equilibrium chamber or cell above the still. The vapor phase emerging from the top of the cell passes into a collector, while the liquid phase is recovered at the bottom of the cell. Thus, when the effluents from the still have been separated and condensed, the weight ratio of 1,1,1-trichloro ethane to 1,2-dichloro ethane is then 34.756/1 in the liquid phase and 65.905/1 in the condensed vapor phase.

The relative pseudo-volatility of 1,1,1-trichloro ethane to 1,2-dichloro ethane is thus 10896/1.

EXAMPLE 3

A mixture of 2-chloro ethanol, 1,1,1-trichloro ethane and 1,2-dichloro ethane of the following composition by weight:

| 2-chloro ethanol | : 70% | |
| 1,1,1-trichloro ethane | : 29.4% | (weight ratio 1,1,1-tri-(chloro ethane/1,2-dichloro |
| 1,2-dichloro ethane | : 0.6% | (ethane = 49/1. | is fed into the still as in Example 2 and partially vaporized. When the effluents have been separated and condensed, the weight ratio of 1,1,1-trichloroethane to 1,2-dichloro ethane is 37.479in the liquid phase and 77.595 in the condensed vapor phase.

The relative pseudo volatility of 1,1,1-trichloro ethane to 1,2-dichloro ethane is thus 2.07/1.

EXAMPLE 4

A mixture of ethyl chloroacetate, 1,1,1-trichloro ethane and 1,2-dichloro ethane of the following composition by weight:

| ethyl chloroacetate | : 70% | |
| 1,1,1-trichloro ethane | : 29.4% | (weight ratio 1,1,1-tri-(chloro ethane/1,2-dichloro |
| 1,2-dichloro ethane | : 0.6% | (ethane = 49/1 | is fed into the still as in Example 2 and partially vaporized. When the effluents have been separated and condensed, the weight ratio of 1,1,1-trichloro ethane to 1,2-dichloro ethane is 40.904/1 in the liquid phase and 61.724/1 in the condensed vapor phase.

The relative pseudo volatility of 1,1,1-trichloro ethane to 1,2-dichloro ethane is thus 1.509/1.

EXAMPLE 5

A mixture of tetramethylurea, 1,1,1-trichloro ethane and 1,2-dichloro ethane of the following composition by weight:

| tetramethylurea | : 70 % | |
| 1,1,1-trichloro ethane | : 29.4% | (weight ratio 1,1,1-tri- |
| | | (chloro ethane/1,2-dichloro |
| 1,2-dichloro ethane | : 0.6% | (ethane = 49/1 | is fed into the same still as in the previous example and partially vaporized as in Example 2.

The relative pseudo volatility of 1,1,1-trichloro ethane to 1,2-dichloro ethane is 1.7/1.

EXAMPLE 6

In the same way as in the previous examples, a mixture of benzaldehyde, 1,1,1-trichloro ethane and 1,2-dichloro ethane of the following composition by weight:

| benzaldehyde | : 70 % | |
| 1,1,1-trichloro ethane | : 29.4% | (weight ratio 1,1,1-tri- |
| | | (chloro ethane/1,2-dichloro |
| 1,2-dichloro ethane | : 0.6% | (ethane = 49/1 | is fed into the still and partially vaporized. When the effluents have been separated and condensed, the weight ratio of 1,1,1-trichloro ethane to 1,2-trichloro ethane to 1,2-dichloro ethane is 45.658/1 in the liquid phase and 76.482 in the condensed vapor phase.

The relative pseduo volatility of 1,1,1-trichloro ethane to 1,2-dichloro ethane is thus 1.675/1.

EXAMPLE 7

A mixture of ethyl acetylacetate, 1,1,1-trichloro ethane and 1,2-dichloro ethane of the following composition by weight:

| ethyl acetylacetate | : 70 % | |
| 1,1,1-trichloro ethane | : 29.4% | (weight ratio 1,1,1-tri- |
| | | (chloro ethane/1,2-dichloro |
| 1,2-dichloro ethane | : 0.6% | (ethane = 49/1 | is fed into the same still as in Examples 2 to 6 and partially vaporized. When the effluents have been separated and condensed, the weight ratio of 1,1,1-trichloro ethane to 1,2-dichloro ethane is 35.666/1 in the liquid phase and 64.351/1 in the condensed vapor phase.

The relative pseudo volatility of 1,1,1-trichloro ethane to 1,2-dichloro ethane is 1.804/1.

EXAMPLE 8

A mixture of salicylaldehyde, 1,1,1-trichloro ethane and 1,2-dichloro ethane of the following composition:

| salicylaldehyde | : 70 % | |
| 1,1,1-trichloro ethane | : 29.4% | (weight ratio 1,1,1-tri- |
| | | (chloro ethane/1,2-dichloro |
| 1,2-dichloro ethane | : 0.6% | (ethane = 49/1 | is fed into the same still as in Examples 2 to 7 and partially vaporized. When the effluents have been separated and condensed, the weight ratio of 1,1,1-trichloro ethane to 1,2-dichloro ethane is 39.906/1 in the liquid phase and 60.964in the condensed vapor phase.

The relative pseudo volatility of 1,1,1-trichloro ethane to 1,2-dichloro ethane is thus 1.527/1.

EXAMPLE 9

A mixture of N-formyl morpholine, 1,1,1-trichloro ethane and 1,2-dichloro ethane of the following composition by weight:

| N-formyl morpholine | : 70 % | |
| 1,1,1-trichloro ethane | : 29.4% | (weight ratio 1,1,1-tri- |
| | | (chloro ethane/1,2-dichloro |
| 1,2-dichloro ethane | 0.6% | (ethane = 49/1 | is subjected to partial vaporization treatment, as in Examples 2 to 8.

The relative pseudo volatility of 1,1,1-trichloro ethane to 1,2-dichloro ethane is then determined and, in this case, is 1.9/1.

EXAMPLE 10

A mixture of δ-butyrolactone, 1,1,1-trichloro ethane and 1,2-dichloro ethane of the following composition by weight:

| butyrolactone | : 70 % | |
| 1,1,1-trichloro ethane | : 29.4% | (weight ratio 1,1,1-tri- |
| | | (chloro ethane/1,2-dichloro |
| 1,2-dichloro ethane | : 0.6% | (ethane = 49/1 | is subjected to partial vaporization treatment, as in Examples 2 to 9.

The relative pseudo volatility of 1,1,1-trichloro ethane to 1,2-dichloro ethane is 1.7/1.

EXAMPLES 11 to 22

Table I which follows shows the relative pseudo volatility of the 1,1,1-trichloro ethane with regard to 1,2-dichloro ethane and summarizes the results obtained with the various organic third compounds used. The procedure is the same as in Examples 2 to 10.

TABLE I

| Examples | Organic Third Compounds | Relative pseudo-volatility *T111/D 12 |
|---|---|---|
| 11 | Hexamethylphosphotriamide | 2.40/1 |
| 12 | Dimethyl sulphate | 1.95/1 |
| 13 | Methyl acetylacetate | 2.20/1 |
| 14 | Tri n-butyl phosphate | 1.75/1 |
| 15 | Benzyl alcohol | 1.75/1 |
| 16 | Methyl monochloroacetate | 1.65/1 |
| 17 | Isopropyl monochloroacetate | 1.60/1 |
| 18 | Tertiary butyl acetylacetate | 1.45/1 |
| 19 | Diethyl oxalate | 1.48/1 |
| 20 | Dimethyl succinate | 1.69/1 |
| 21 | Methylisobutylketone | 1.45/1 |
| 22 | N-heptanal | 1.30/1 |

*T 111/D 12 = 1,1,1-trichloro ethane/1,2-dichloro ethane

In a comparative test, a mixture of 1,1,1-trichloro ethane and 1,2-dichloro ethane, comprising 98% by weight of 1,1,1-trichloro ethane and 2% by weight of 1,2-dichloro ethane (weight ratio = 49/1) but without any organic third compound, is subjected to partial vaporization as in Examples 2 to 10 above.

When the effluents have been separated and condensed, the weight ratio of 1,1,1-trichloro ethane to 1,2-dichloro ethane is 48.505/1 in the liquid phase and 53.348/1 in the vapor phase collected. The relative volatility of 1,1,1-trichloro ethane to 1,2-dichloro ethane is thus only 1.1/1.

EXAMPLES 23 to 30

A mixture of an organic third compound, triclorothylene and 1,2-dichloro ethane of the following composition by weight:

| | | |
|---|---|---|
| organic third compound | : 50 % | |
| trichloroethylene | : 22.5% | (weight ratio trichloro-(ethylene/1,2-dichloro |
| 1,2-dichloro ethane | : 27.5% | (ethane = 0.8182/1 (azeotropic mixture) | is placed in the same still as in Example 10.

Partial vaporization of the mixture followed by separation and condensation of the effluents, was carried out as in the previous examples. Table II summarizes the results thus obtained.

TABLE II

| Examples | Organnic Third Compounds | Relative pseudo-volatility * T111/D 12 |
|---|---|---|
| 23 | 2-chloro ethanol | 1.322/1 |
| 24 | Acetic anhydride | 1.356/1 |
| 25 | Ethyl chloroacetate | 1.143/1 |
| 26 | Benzaldehyde | 1.134/1 |
| 27 | Ethyl acetylacetate | 1.260/1 |
| 28 | Salicylaldehyde | 1.101/1 |
| 29 | γ-butyrolactone | 1.547/1 |
| 30 | N-formyl morpholine | 1.444/1 |

* Tri/D 12 = Trichloroethylene/1,2-dichloro ethane

We claim:

1. A method of at least partially separating chlorinated aliphatic $C_1$ to $C_3$ hydrocarbons from mixtures of at least two of the chlorinated hydrocarbons by extractive distillation, comprising subjecting the mixture of the chlorinated hydrocarbons to extractive distillation in contact with one or more organic third compounds having a boiling point higher than that of the substances to be separated, the extractive distillation being carried out at a temperature below the boiling point temperature for the third compound, in which the third compound is selected from the group consisting of methyl, ethyl, normal propyl and isopropyl mono and dichloroacetates; benzyl alcohol; salicylaldehyde, benzaldehyde, n-heptanal, methylisobutylketone, tetramethylurea, γ-butyrolacetone; normal propyl, isopropyl, normal, secondary and tertiary butyl acetylacetates; diethyl oxalate, dimethyl succinate and preferably methyl and ethyl acetylacetates; acetic anhydride, N-formylmorpholine, 2-chloro ethanol, hexamethylphosphotriamide, dimethyl sulphate and normal tributyl and triisobutyl phosphates, and recovering as overhead a separated distillate stream which contains a higher proportion of one of the chlorinated hydrocarbons then said mixture and a bottoms stream containing said third compound and a higher proportion of the other chlorinated hydrocarbons than said mixture.

2. The method as claimed in claim 1, in which the mixture of chlorinated aliphatic hydrocarbons comprises 1,2-dichloro ethane and 1,1,1-trichloro ethane.

3. The method as claimed in claim 1, in which the mixture of chlorinated aliphatic hydrocarbons comprises trichloroethylene and 1,2-dichloro ethane.

4. The method as claimed in claim 1, in which the mixture of chlorinated aliphatic hydrocarbons comprises perchloroethylene and 1,1,2-trichloro ethane.

5. The method as claimed in claim 1, in which the mixture of chlorinated aliphatic hydrocarbons comprises carbon tetrachloride and 12-dichloro ethane.

6. The method as claimed in claim 1, in which the proportion of organic third compound used in the mixture of chlorinated aliphatic hydrocarbons is at least 10% by weight.

7. The method as claimed in claim 1, in which the organic third compound is present in the amount within the range of one to three times the weight of the mixture.

8. The method as claimed in claim 1, in which the extractive distillation is carried out at atmospheric pressure.

9. The method as claimed in claim 1, in which the extractive distillation is carried out at a pressure below atmospheric.

10. The method as claimed in claim 1, in which the extractive distillation is carried out under partial to high pressure.

11. The method as claimed in claim 1, in which the organic third compound is recovered at a pressure below that used for extractive distillation of the chlorinated hydrocarbons.

12. The method as claimed in claim 1 which includes the step of subjecting the bottom stream to distillation to separate and recover the chlorinated hydrocarbon as a overhead from the third compound, and recycling the third compound to the extractive distillation.

13. The method as claimed in claim 1 which includes the step of condensing the overhead from the extractive distillation to produce a condensate in which the one chlorinated hydrocarbon is present in a concentration higher than in the original mixture.

* * * * *